United States Patent
Sharma et al.

(10) Patent No.: US 9,717,426 B2
(45) Date of Patent: Aug. 1, 2017

(54) OPTICAL RECEIVER CHAIN FOR COMPONENTS OF A PHOTOPLETHYSMOGRAPH SIGNAL

(71) Applicant: Texas Instruments Incorporated, Dallas, TX (US)

(72) Inventors: Ajit Sharma, Dallas, TX (US); Sriram Narayanan, Richardson, TX (US); Srinath Mathur Ramaswamy, Murphy, TX (US); Arup Polley, Richardson, TX (US); Seung Bae Lee, Allen, TX (US); Wen Li, McKinney, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 172 days.

(21) Appl. No.: 14/837,179

(22) Filed: Aug. 27, 2015

(65) Prior Publication Data
US 2016/0235313 A1  Aug. 18, 2016

Related U.S. Application Data

(60) Provisional application No. 62/115,756, filed on Feb. 13, 2015.

(51) Int. Cl.
*A61B 5/024* (2006.01)
*A61B 5/00* (2006.01)

(52) U.S. Cl.
CPC ........ *A61B 5/02427* (2013.01); *A61B 5/6826* (2013.01); *A61B 5/7228* (2013.01); *A61B 2562/0238* (2013.01)

(58) Field of Classification Search
CPC .............. A61B 5/02427; A61B 5/7228; A61B 2562/0238; A61B 5/6827
See application file for complete search history.

(56) References Cited

U.S. PATENT DOCUMENTS

| | | | | |
|---|---|---|---|---|
| 4,258,719 A | * | 3/1981 | Lewyn | A61B 5/02416 307/650 |
| 5,800,348 A | * | 9/1998 | Kaestle | G01N 21/3151 600/322 |
| 2003/0163034 A1 | * | 8/2003 | Dekker | A61B 5/0205 600/372 |

(Continued)

FOREIGN PATENT DOCUMENTS

| | | |
|---|---|---|
| EP | 0319160 | 7/1989 |
| RU | 2306841 | 9/2007 |

OTHER PUBLICATIONS

International Search Report in corresponding PCT Patent Application No. PCT/US2016/017994, mailed Jun. 20, 2016 (2 pages).

(Continued)

*Primary Examiner* — Catherine Voorhees
(74) *Attorney, Agent, or Firm* — John R. Pessetto; Charles A. Brill; Frank D. Cimino

(57) ABSTRACT

The circuitry of an optical receiver reduces the ambient DC component and the pleth DC component to leave a pleth signal with substantially only a pleth AC component. The circuitry also provides gain control and can provide transmit power control to change the range of the pleth AC component to occupy a desired input range of an analog-to-digital converter.

20 Claims, 10 Drawing Sheets

(56) References Cited

U.S. PATENT DOCUMENTS

2014/0058229 A1* 2/2014 Su .................. A61B 5/7214
600/323

OTHER PUBLICATIONS

E.S. Winokur, et al., "A Low-Power, Dual-Wavelength Photoplethysmogram (PPG) SoC with Static and Time-Varying Interferer Removal", IEEE Trans Biomed Circuits Syst, vol. PP, Issue 99, Oct. 2014.

* cited by examiner

OPTICAL RECEIVER CHAIN FOR COMPONENTS OF A PHOTOPLETHYSMOGRAPH SIGNAL

CROSS-REFERENCE TO RELATED APPLICATION

This application claims priority to U.S. Provisional Application Ser. No. 62/115,756 filed Feb. 13, 2015, entitled DAC-BASED RECEIVE CHAIN FOR BODY PARAMETER MEASUREMENTS, naming Ajit Sharma et al. as inventors, which is hereby fully incorporated herein by reference for all purposes.

BACKGROUND

The disclosures herein relate generally to electronic circuitry, and more particularly to an optical receiver chain for components of a photoplethysmograph signal.

A plethysmograph is a device that measures changes in volume, typically changes in the volume of blood or the volume of air within a tested portion of a human body. A photoplethysmograph ("PPG") is a plethysmograph that uses a beam of light to detect changes in the volume. A pulse oximeter is a type of PPG that measures changes in the volume of arterial blood within the tested portion of the body to determine an oxygen saturation level (SpO2). The change can be measured with each heart-beat.

In pulse-oximetry/optical heart rate monitoring ("HRM"), an optical transmitter uses one or more light-emitting diodes ("LEDs") to emit light onto a body, where changes in arterial blood volume modulate the intensity of the LED light. An optical receiver receives the modulated LED light (at single or multiple wavelengths) via a photo detector, such as a photodiode/photo-transistor or avalanche photodiode ("APD"), and generates a pleth signal in response to the modulated LED light. The oxygen saturation level (SpO2) can then be obtained from the pleth signal. In at least one example, the LED is pulsed to save power.

Pulse oximeters can operate as transmission-type devices or reflectance-type devices. With transmission-type devices, the LED light passes through the body before the LED light is received by the photo detector. With reflectance-type devices, the LED light reflects off of the body before the LED light is received by the photo detector.

FIGS. 1A-1B are diagrams of a conventional transmission-type pulse oximeter 100. As shown in FIGS. 1A-1B, pulse oximeter 100 includes an LED 110 that generates pulsed light 112, an LED 114 that generates pulsed light 116, and a photo detector 118 that detects the pulsed lights 112 and 116. LED 110 generates the pulsed light 112 having a first frequency, such as infrared (IR), while LED 114 generates the pulsed light 116 having a second frequency, such as red (R). Also, conventional LEDs, such as LED 110 and LED 114, also generate a minor amount of off-axis light, which is scattered and detected by photo detector 118.

As shown in FIG. 1A, the LEDs 110/114 and photo detector 118, which are connected to a processing chip 120, are spaced apart and positioned to face each other. As shown in FIG. 1B, as a transmission-type device, the pulsed lights 112 and 116 pass through a tested portion of a human body, such as a finger 122, before being received by photo detector 118.

FIGS. 2A-2B are diagrams of a conventional reflectance-type pulse oximeter 200. As shown in FIGS. 2A-2B, as with pulse oximeter 100, pulse oximeter 200 includes an LED 210 that generates pulsed light 212, an LED 214 that generates pulsed light 216, and a photo detector 218 that detects the pulsed lights 212 and 216. LED 210 generates the pulsed light 212 having a first frequency, such as infrared (IR), while LED 214 generates the pulsed light 216 having a second frequency, such as red (R). Also, LED 210 and LED 214 generate a minor amount of off-axis light, which is scattered and detected by photo detector 218.

As shown in FIG. 2A, the LEDs 210/214 and photo detector 214, which are connected to a processing chip 220, lie adjacent to each other and face in the same direction. As shown in FIG. 2B, as a reflectance-type device, the pulsed lights 212 and 216 reflect off of a tested portion of the body, such as a finger 222, before being received by photo detector 218.

The pleth signal generated by a pulse oximeter has an ambient DC component, a pleth DC component, and a pleth AC component that rides on the pleth DC component. The ambient DC component results from ambient conditions. Non-hospital environments (such as wearable fitness trackers and mobile patient monitoring bands) are difficult to control, so many factors can affect the ambient DC component of the pleth signal. The ambient DC component (due to biological drifts or environmental variations) is exacerbated in wearable/portable applications (e.g., fitness tracking), where ambient conditions are not well-controlled, such as: (a) sudden shift from sunlight to shade; and (b) random or uncontrolled motion (e.g., biking and running).

FIG. 3 is a diagram of a conventional pulse oximeter system 300. As shown in FIG. 3, pulse oximeter system 300 includes an optical transmitter 310 that generates pulsed light 312. Optical transmitter 310 includes a LED 314, a current source 316 that sinks current from LED 314, and a switch 318 that opens and closes to generate the pulsed light 312.

System 300 also includes a channel 320, which includes all of the conditions that can affect the pulsed light 312. Changes in the arterial blood volume within the tested portion of a human body can be represented by a body signal generator 322 that outputs a body signal BS, while the interaction of the body with the pulsed light 312 can be represented by a modulator 324 that amplitude modulates the pulsed light 312 with the body signal BS to generate a pulsed body-modified light 326. Also, the interaction of the body with the body-modified light 326 dims the body-modified light 326, and can be represented by an attenuater 330 that reduces the intensity of the pulsed body-modified light 326 to produce a pulsed attenuated body-modified light 332.

Further, the ambient environmental conditions can be represented by an ambient signal generator 334 that outputs an ambient DC voltage VA, while the interaction of the environmental conditions with the attenuated body-modified light 332 can be represented by an adder 336 that adds the ambient DC voltage VA to the attenuated body-modified light 332 to form a pulsed modulated light 338, which has a DC offset due to the ambient DC voltage VA.

System 300 additionally includes an optical receiver 340 that receives the pulsed modulated light 338, and generates a sampled pleth signal SS in response to the pulsed modulated light 338. Receiver 340 includes a photo detector 342 that generates a photo current IP in response to the pulsed modulated light 338, and a transimpedance amplifier 344 that converts the photo current IP into a voltage VP.

Receiver 340 also includes a switch 346 that opens and closes, and a resistor/capacitor combination 348 that samples and holds the voltage VP when switch 346 is closed and opened to generate the sampled pleth signal SS. Switch 346 is closed during all or part of the time that switch 318 is closed. An analog-to-digital converter ("ADC") then digitizes the sampled pleth signal SS.

FIG. 4 is a diagram of a conventional pleth signal PL. As shown in FIG. 4, the pleth signal PL has an ambient DC component 410, a pleth DC component 412, and a pleth AC component 414. The ambient DC component 410 is a pedestal or baseline, which exists even when the LED is turned OFF. The ambient DC component 410 can be caused by varying ambient illumination conditions or biological processes, and it may vary based on motion artifacts.

The pleth DC component 412 results from variations in light absorption by the structures within the tested portion of the body. Some structures within the body, such as the skin and nonpulsatile blood, absorb a constant amount of light, which produces the pleth DC component 412, while the pulsating arterial blood flow absorbs a variable amount of light, which produces the pleth AC component 414.

The pleth AC component 414 rides over the pleth DC component 412, which is proportional to applied LED illumination. In the HRM example, the useful signal for HRM is obtained from the pleth AC component 414 that rides over the large DC signal, which includes an ambient DC component 410 and a pleth DC component 412. The pleth AC component 414 (from which the oxygen saturation level (SpO2) or heart rate information is obtained) is proportional to the pleth DC component 412. The ratio of the AC to DC component is referred to as the Perfusion Index.

The pleth AC component 414 is relatively small, but can be increased by increasing the transmit intensity of the light output by LED 314. Increasing the transmit intensity of the light output by LED 314 increases the magnitude of the pleth AC component 414 more than the magnitude of the pleth DC component 412. However, only small increases can typically be made without saturating the ADC that digitizes the sampled pleth signal SS.

The ambient DC component and the pleth DC component consume a significant portion of the ADC's dynamic range for PPG measurement and is considered an "interferer." If the ADC is designed with a wide dynamic range to accommodate the signal plus all possible sources of DC offset, then it would be energy inefficient and unsuitable for portable applications.

Some techniques use a single point for ambient cancellation after a front-end transimpedance amplifier ("TIA"). But those techniques are insufficient, because the signal is lost if the TIA saturates. Additional techniques apply a single DC offset correction point at the TIA's input. But those techniques incur a noise penalty in correcting DC across a wide range (e.g., ambient level plus pleth DC level). Such noise penalty imposes stringent requirements on an input current digital-to-analog converter ("DAC"). Other techniques correct DC level by changing the LED level. A lower LED current level decreases the pleth DC level. However, while those techniques directly impact the pleth level, so they can affect the AC component itself, because the AC component is proportional to the DC component, thereby reducing the receiver signal-to-noise ratio (SNR).

SUMMARY

The present disclosure provides circuitry for an optical receiver that reduces the ambient and pleth DC components of a pleth signal. The circuitry includes a photo detector to receive ambient light that has an ambient intensity and, in response thereto, output a first signal on at least one first line having a first magnitude that represents the ambient intensity. The photo detector to also receive pulsed light that has a pulsed intensity and, in response thereto, output a second signal on the at least one first line having a second magnitude that represents the pulsed intensity without the ambient intensity. The second magnitude of the second signal has a pleth DC component and a pleth AC component. The circuitry also includes a demodulation circuit coupled to the photo detector. The demodulation circuit to sample and hold the first signal, and output a third signal on at least one second line whose magnitude represents the first magnitude of the first signal. The demodulation circuit to also sample and hold the second signal, and output a fourth signal on the at least one second line whose magnitude represents the second magnitude of the second signal. The magnitude of the fourth signal has a pleth DC component that represents the pleth DC component of the second signal, and a pleth AC component that represents the pleth AC component of the second signal.

A method of operating circuitry for an optical receiver includes receiving ambient light that has an ambient intensity and, in response thereto, outputting a first signal having a first magnitude that represents the ambient intensity. The method also includes receiving pulsed light that has a pulsed intensity and, in response thereto, outputting a second signal having a second magnitude that represents the pulsed intensity without the ambient intensity. The second magnitude of the second signal has a pleth DC component and a pleth AC component. The method further includes sampling and holding the first magnitude of the first signal, and outputting a third signal having a magnitude that represents the first magnitude of the first signal. The method additionally includes sampling and holding the second magnitude of the second signal, and outputting a fourth signal with a magnitude that represents the second magnitude of the second signal. The magnitude of the fourth signal has a pleth DC component that represents the pleth DC component of the second signal, and a pleth AC component that represents the pleth AC component of the second signal.

DETAILED DESCRIPTION

Figure 1A:
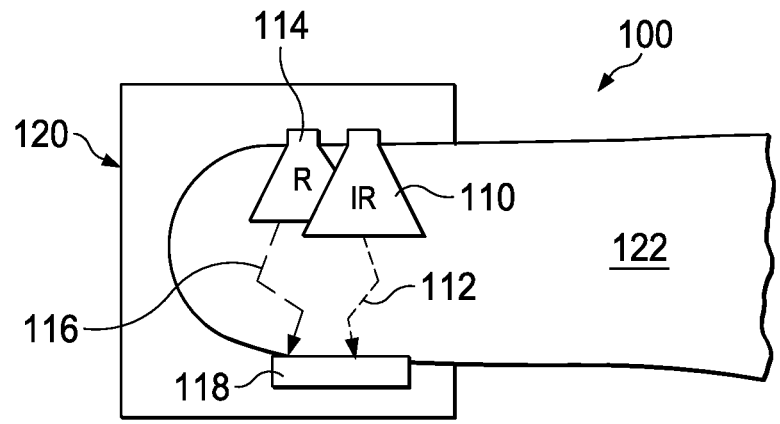
FIGS. 1A-1B (prior art) are diagrams of a conventional transmission-type pulse oximeter 100.
Figure 1B:
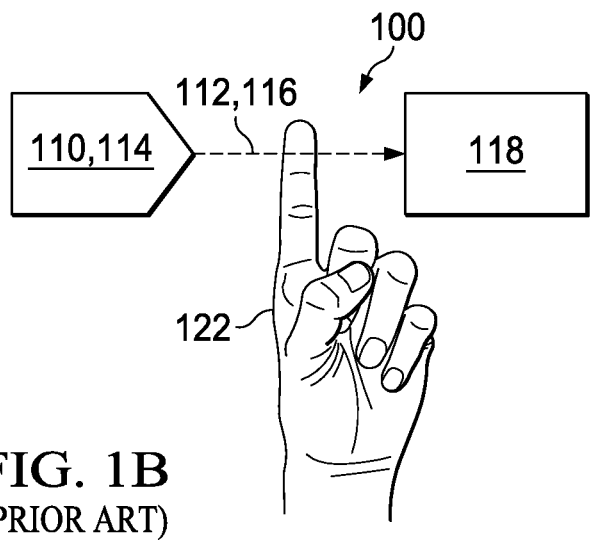
Figure 2A:
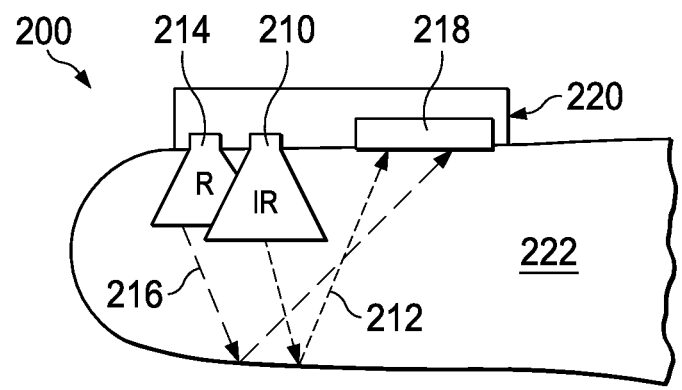
FIGS. 2A-2B (prior art) are diagrams of a conventional reflectance-type pulse oximeter 200.
Figure 2B:
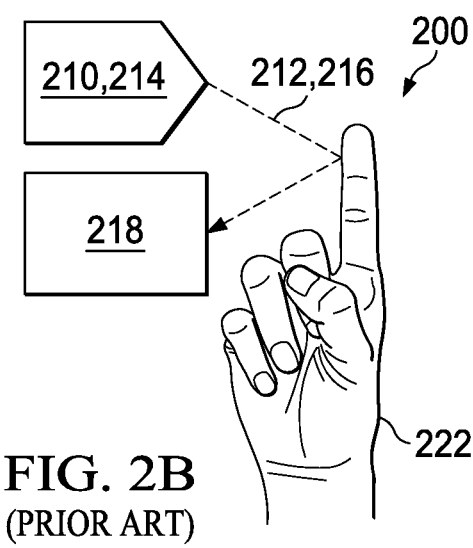
Figure 3:
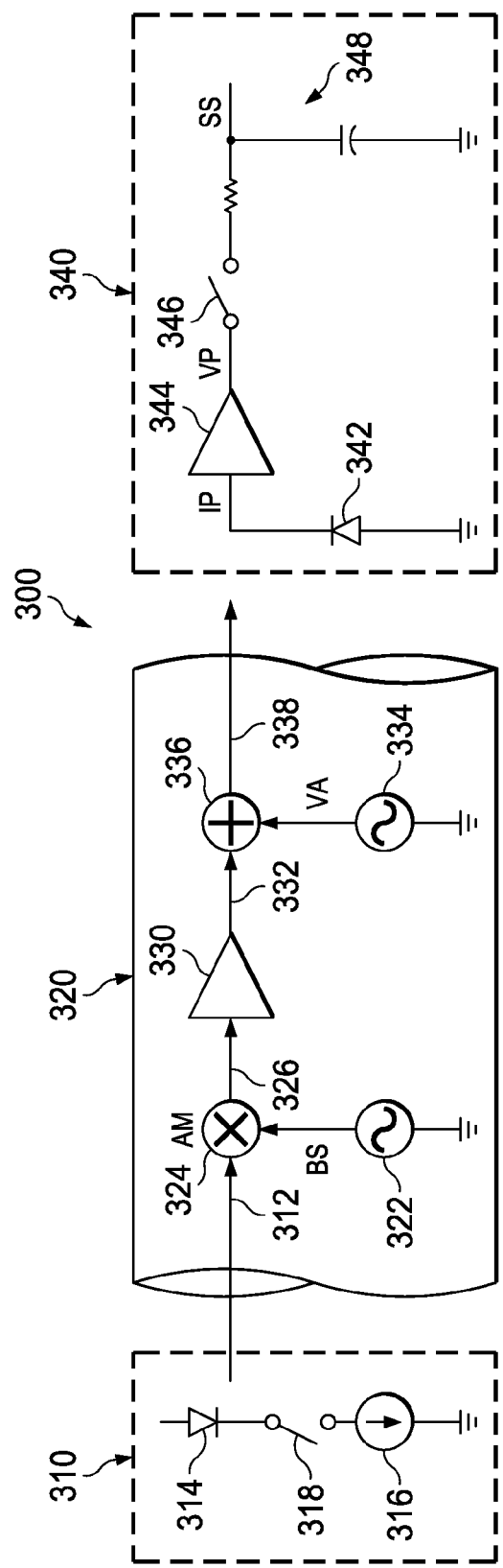
FIG. 3 (prior art) is a diagram of a conventional pulse oximeter system 300.
Figure 4:
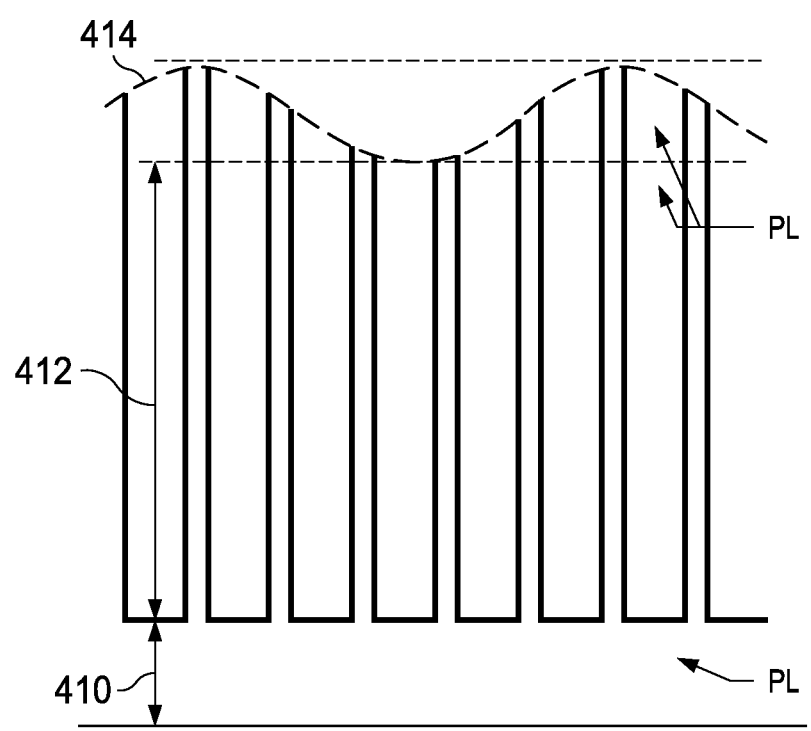
FIG. 4 (prior art) is a diagram of a conventional pleth signal PL.
Figure 5:
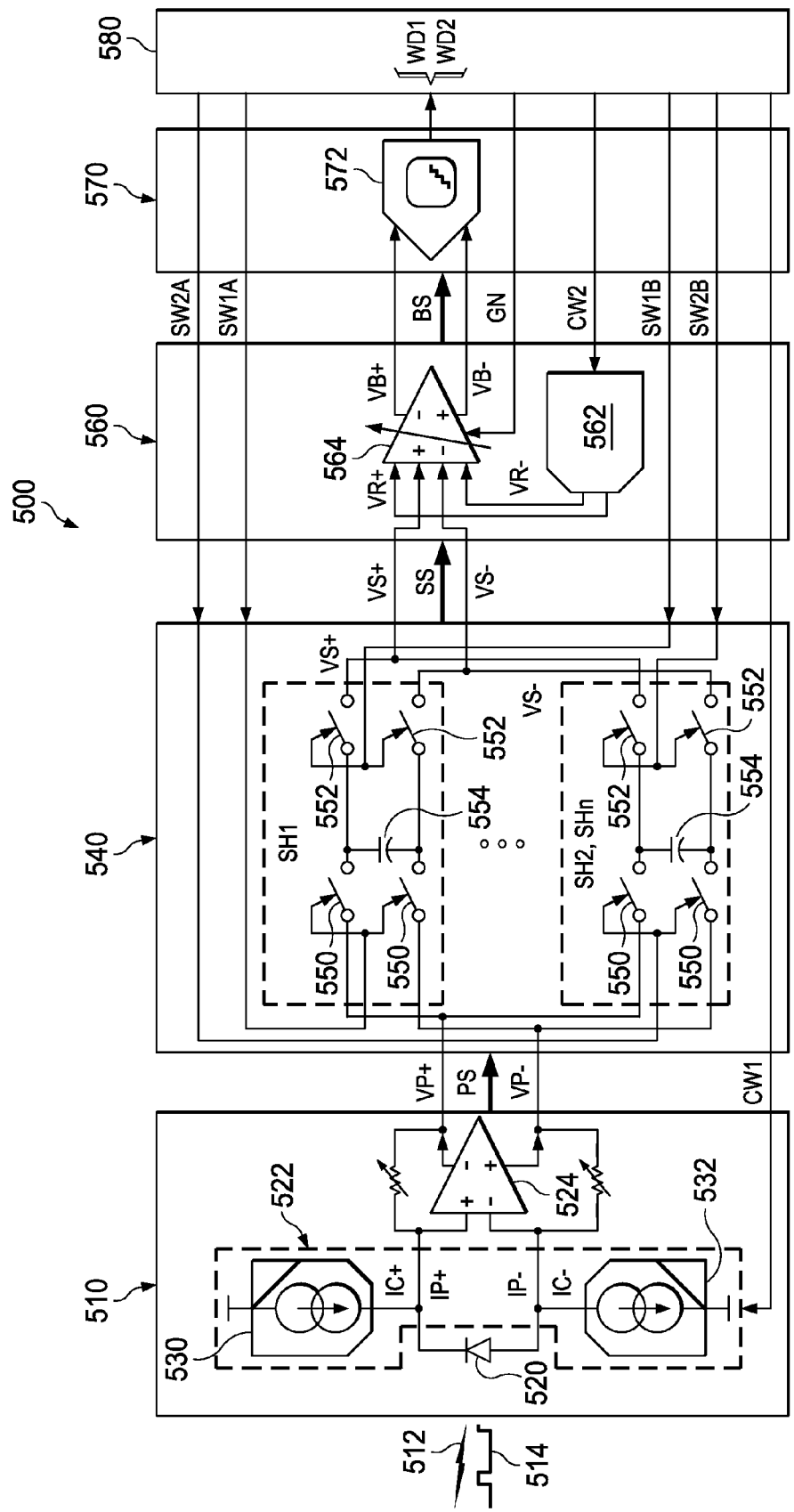
FIG. 5 is a schematic diagram of circuitry for an optical receiver of the example embodiments.

FIG. 5 is a schematic diagram of circuitry, indicated generally at 500, for an optical receiver. As described in greater detail below, the circuitry 500 reduces the ambient DC component and the pleth DC component of a pleth signal to identify a pleth AC component. After being subject to increased gain and/or an increased LED transmit power, the pleth AC component occupies the desired input range of an analog-to-digital converter.

As shown in FIG. 5, circuitry 500 includes a photo detector 510 that responds to light. Photo detector 510 receives ambient light 512, detects the intensity of the ambient light 512 (the ambient intensity), and outputs a first signal on line(s) PS having a first magnitude that represents the ambient intensity. The ambient intensity is generally substantially constant over a short period of time, such as minutes, but gradually changes over a longer period of time, such as hours.

Also, photo detector 510 receives pulsed light 514, detects the intensity of the pulsed light 514 (the pulsed intensity, which is greater than the ambient intensity), and outputs a second signal on line(s) PS having a second magnitude that represents the pulsed intensity without the ambient intensity. The ambient intensity has a single component, which is an ambient DC intensity component. In contrast, the pulsed intensity has three components, which are: the ambient DC intensity component, a pleth DC intensity component, and a pleth AC intensity component.

Reducing the pulsed intensity by the ambient intensity substantially removes the ambient DC intensity component from the pulsed intensity, leaving substantially only the pleth DC intensity component and the pleth AC intensity component. To reduce the pulsed intensity by the ambient intensity, photo detector 510 reduces a second magnitude (which represents the pulsed intensity) by a first magnitude (which represents the ambient intensity as an ambient DC correction word CW1).

The first magnitude of the first signal on line(s) PS has a single component, which is an ambient DC component that represents the ambient DC intensity component. The second magnitude of the second signal on line(s) PS has substantially only two components, which are: a pleth DC component that represents the pleth DC intensity component, and a pleth AC component that represents the pleth AC intensity component. The second signal on line(s) PS is formed by reducing the pulsed intensity by the ambient intensity, so that photo detector 510 substantially removes the ambient DC intensity component before outputting the second signal on line(s) PS.

In the FIG. 5 example, photo detector 510 is implemented with a photodiode 520, an ambient DC correction circuit 522, and a transimpedance amplifier 524. Photodiode 520 generates and outputs a pair of differential currents IP+ and IP− in response to ambient light 512 and pulsed light 514 at various times. Accordingly, at various times, the differential currents IP+ and IP− have first magnitudes that represent the ambient intensity, and second magnitudes that represent the pulsed intensity. The first magnitudes of IP+ and IP− have only a single component, which is an ambient DC component. The second magnitudes of IP+ and IP− have three components, which are: the ambient DC component, a pleth DC component, and a pleth AC component.

Ambient DC correction circuit 522, which is coupled to photo diode 520, sources and sinks a pair of correction differential currents IC+ and IC− that have magnitudes defined by the ambient DC correction word CW1. As shown in the FIG. 5 example, ambient DC correction circuit 522 can be implemented with a current-sourcing digital-to-analog (D/A) converter 530 and a current-sinking D/A converter 532, which are both coupled to photo diode 520.

Current-sourcing D/A converter 530 receives the ambient DC correction word CW1, and sources the correction differential current IC+ in response to the ambient DC correction word CW1. Current-sinking D/A converter 532 receives the ambient DC correction word CW1, and sinks the correction differential current IC− in response to the ambient DC correction word CW1. IC+ and IC− combine with IP+ and IP− to reduce the second magnitudes of IP+ and IP− by the magnitudes of IC+ and IC−, in order to form corrected magnitudes of IP+ and IP−.

Transimpedance amplifier 524, which is coupled to photo diode 520 and ambient DC correction circuit 522, converts the corrected magnitudes of IP+ and IP− into a pair of differential voltages on lines VP+ and VP− having at various times: (a) first magnitudes that represent the first magnitudes of IP+ and IP−; and (b) second magnitudes that represent the corrected magnitudes of IP+ and IP−. In the example of FIG. 5, the first and second signals on line(s) PS are formed by the differential voltages on lines VP+ and VP−.

As further shown in FIG. 5, circuitry 500 also includes a demodulation circuit 540 that is coupled to photo detector 510. Demodulation circuit 540 samples and holds the first signal on line(s) PS, and outputs a third signal on line(s) SS whose magnitude represents the first magnitude of the first signal on line(s) PS. Circuit 540 additionally samples and holds the second signal on line(s) PS, and outputs a fourth signal on line(s) SS whose magnitude represents the second magnitude of the second signal on line(s) PS.

The magnitude of the third signal on line(s) SS has an ambient DC component that represents the ambient DC component of the first signal on line(s) PS. The magnitude of the fourth signal on line(s) SS has a pleth DC component that represents the pleth DC component of the second signal on line(s) PS, and a pleth AC component that represents the pleth AC component of the second signal on line(s) PS.

In the FIG. 5 example, demodulation circuit 540 is implemented with a series of SH sub-circuits SH1-SHn that are coupled to transimpedance amplifier 524. This example shows two SH sub-circuits SH1 and SH2. Each SH sub-circuit SH1-SHn is implemented with a pair of input switches 550 that receive the differential voltages on lines VP+ and VP−, and a pair of output switches 552 that output a pair of sampled differential voltages VS+ and VS−.

The pair of input switches 550 of SH sub-circuit SH1 are controlled by a switch signal SW1A, while the pair of output switches 552 are controlled by a switch signal SW1B. The pair of input switches 550 of SH sub-circuit SH2 are controlled by a switch signal SW2A, while the pair of output switches 552 are controlled by a switch signal SW2B.

Also, each SH sub-circuit SH1-SHn is implemented with a capacitor 554 for storing a charge. The top plate of each capacitor 554 is coupled to a top input switch 550 and a top output switch 552. The bottom plate of each capacitor 554 is coupled to a bottom input switch 550 and a bottom output switch 552.

When the input switches 550 of a SH sub-circuit close, the differential voltages on lines VP+ and VP− are sampled, and then held across the capacitor 554 of the SH sub-circuit when the input switches 550 open. When the output switches 552 of the SH sub-circuit close, the differential voltages on lines VP+ and VP− held across the capacitor 554 of the SH sub-circuit are output as VS+ and VS−.

SH sub-circuit SH1 samples and holds the first magnitudes of the differential voltages on lines VP+ and VP−, and outputs VS+ and VS− having first magnitudes that represent the first magnitudes of the differential voltages on lines VP+ and VP−. SH sub-circuit SH2 samples and holds the second magnitudes of the differential voltages on lines VP+ and VP−, and outputs VS+ and VS− having second magnitudes that represent the second magnitudes of the differential voltages on lines VP+ and VP−. In the implementation illustrated in FIG. 5, the third and fourth signals on line(s) SS are output as VS+ and VS−.

As additionally shown in FIG. 5, circuitry 500 further includes a buffer 560 that is coupled to demodulation circuit 540. Buffer 560 receives the magnitude of the third signal on line(s) SS, and outputs a pleth signal BS having a first magnitude that represents the magnitude of the third signal on line(s) SS. Buffer 560 also receives the magnitude of the fourth signal on line(s) SS, reduces the magnitude of the fourth signal on line(s) SS by a magnitude, which is defined by a pleth DC correction word CW2, and outputs the pleth signal BS having a second magnitude that represents substantially only the pleth AC component of the fourth signal on line(s) SS (a small pleth DC component can exist to provide an error margin). The pleth DC correction word CW2 represents the pleth DC component.

The first magnitude of the pleth signal BS has a single component, which is an ambient DC component. The second magnitude of the pleth signal BS has substantially only one component, which is a pleth AC component (a small pleth DC component can exist to provide an error margin). Reducing the magnitude of the fourth signal on line(s) SS by the pleth DC correction word CW2 substantially removes the pleth DC component from the pleth signal BS, leaving substantially only the pleth AC component. Buffer 560 reduces the pleth DC component by reducing a charge/voltage, which represents the magnitude of the fourth signal on line(s) SS, by a charge/voltage, which represents the pleth DC component as defined by the pleth DC correction word CW2.

In the FIG. 5 example, buffer 560 is implemented with a D/A charge/voltage converter 562 that generates and outputs a pair of correction differential charges/voltages VR+ and VR− that have magnitudes which are defined by the pleth DC correction word CW2. Buffer 560 is also implemented with an amplifier 564 that is coupled to D/A charge/voltage converter 562.

Amplifier 564 amplifies the first magnitudes of VS+ and VS− to form the first magnitudes of a pair of pleth differential voltages VB+ and VB−. Amplifier 564 also reduces the second magnitudes of VS+ and VS− by an amount defined by the magnitudes of VR+ and VR− (which are defined by the pleth DC correction word CW2) to form the second magnitudes of VB+ and VB−. In the implementation illustrated in FIG. 5, the pleth signal BS is output as VB+ and VB−.

Circuitry 500 further includes an analog-to-digital (A/D) converter 570 that is coupled to buffer 560. A/D converter 570 digitizes the first magnitude of the pleth signal BS to form a first digital word WD1 that represents the first magnitude of the pleth signal BS. A/D converter 570 also digitizes the second magnitude of the pleth signal BS to form a second digital word WD2 that represents the second magnitude of the pleth signal BS. For example, A/D converter 570 can have an input range of 0V-1V.

As shown in FIG. 5, A/D converter 570 can be implemented with a differential A/D converter 572 that receives VB+ and VB−. Differential A/D converter 572 digitizes the first magnitudes of VB+ and VB− to form the first digital word WD1. Differential A/D converter 572 also digitizes the second magnitudes of VB+ and VB− to form the second digital word WD2.

Also, circuitry 500 includes a controller 580 that is coupled to photo detector 510, buffer 560, and A/D converter 570. Controller 580 generates the ambient DC correction word CW1, which represents the ambient intensity, in response to the first digital word WD1, and outputs the ambient DC correction word CW1 to photo detector 510. Controller 580 also generates the pleth DC correction word CW2, which defines the amount that the magnitude of the fourth signal on line(s) SS is to be reduced to reduce the pleth DC component, in response to the second digital word WD2, and outputs the pleth DC correction word CW2 to buffer 560.

Figure 6A:
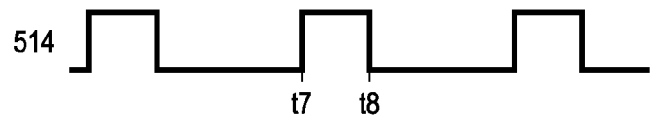
FIGS. 6A-6G are timing diagrams of an operation of the circuitry of FIG. 5.
Figure 6B:
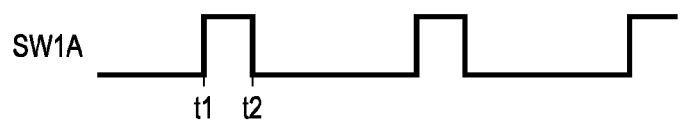
Figure 6C:
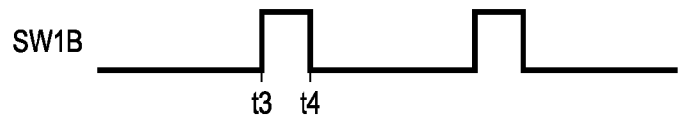
Figure 6D:
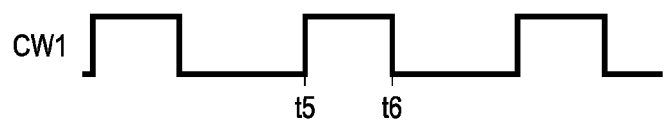
Figure 6E:
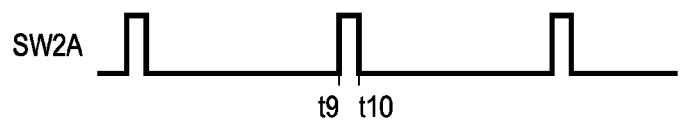
Figure 6F:
Figure 6G:
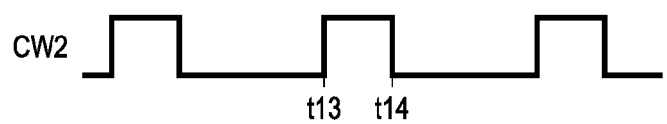

FIGS. 6A-6G are timing diagrams of an operation of the circuitry 500 of FIG. 5. FIG. 6A is a timing diagram of the pulsed light 514. FIG. 6B is a timing diagram of switch signal SW1A. FIG. 6C is a timing diagram of switch signal SW1B. FIG. 6D is a timing diagram of the ambient DC correction word CW1. FIG. 6E is a timing diagram of switch signal SW2A. FIG. 6F is a timing diagram of switch signal SW2B. FIG. 6G is a timing diagram of the pleth DC correction word CW2.

As shown in FIG. 6A, a light-emitting diode (LED) transmits pulsed light 514. In this example, controller 580 controls the transmit timing of pulsed light 514, but can alternately be notified of the transmit timing of pulsed light 514 by an external signal. Knowing the transmit timing of pulsed light 514, controller 580 closes and opens the input and output switches 550 and 552 of the SH sub-circuits SH1-SHn during times that correspond with the on and off times of the LED.

As shown in FIG. 6B, when no pulsed light 514 is transmitted by the LED and ambient light 512 is received by photo diode 520, controller 580 outputs the switch signal SW1A from time t1 to time t2. The top and bottom input switches 550 of SH sub-circuit SH1 close at time t1 in response to the switch signal SW1A, and then open at time t2, which causes capacitor 554 to sample and hold the first magnitudes of the differential voltages on lines VP+ and VP−, which represent the intensity of the ambient light 512.

After this, as shown in FIG. 6C, controller 580 outputs the switch signal SW1B from time t3 to time t4. The top and bottom output switches 552 of SH sub-circuit SH1 close at time t3 in response to the switch signal SW2, and then open at time t4, which causes the capacitor 554 to output the differential voltages on lines VP+ and VP− to buffer 560 as VS+ and VS−, which have first magnitudes that represent the first magnitudes of the differential voltages on lines VP+ and VP−, which represent the intensity of the ambient light 512.

Buffer 560 amplifies the first magnitudes of the sampled differential voltages VS+ and VS− to output VB+ and VB−. The pleth differential voltages VB+ and VB− have first magnitudes that represent the first magnitudes of the sampled differential voltages VS+ and VS−. A/D converter 570 digitizes the first magnitudes of the pleth differential voltages VB+ and VB−, and outputs the first digital word WD1, which represents the first magnitudes of VB+ and VB−, which represents the intensity of the ambient light 512.

Controller 580 uses the first digital word WD1 to generate and output the ambient correction word CW1, which can be generated in various ways. For example, because the first digital word WD1 represents the first magnitudes of VB+ and VB−, which represent the ambient intensity, controller 580 can generate the ambient DC correction word CW1 by converting the first digital word WD1 directly into the ambient DC correction word CW1. Alternately, controller

580 can generate the ambient DC correction word CW1 by using a number of the first digital words WD1. For example, the ambient DC correction word CW1 can be equal to the average first magnitudes of VB+ and VB− of the last 6 first digital words WD1.

As shown in FIG. 6D, controller 580 outputs the ambient DC correction word CW1 to photo detector 510 from time t5 to time t6. The ambient DC correction word CW1 causes ambient DC correction circuit 522 to source and sink IC+ and IC−, which then combine with IP+ and IP− to reduce the second magnitudes of IP+ and IP− to form corrected magnitudes of IP+ and IP−. The corrected magnitudes of IP+ and IP− correspond substantially with the removal of the ambient intensity from the pulsed intensity. The removal of the ambient intensity from the pulsed intensity leaves the pleth DC component and the pleth AC component.

As shown in FIG. 6A, the LED transmits the pulsed light 514 with the pulsed intensity from time t7 to time t8. During this time, transimpedance amplifier 524 converts the corrected magnitudes of IP+ and IP− into the second magnitudes of VP+ and VP−.

As shown in FIG. 6E, when pulsed light 514 is transmitted by the LED and received by photo diode 520 from time t7 to time t8, controller 580 outputs the switch signal SW2A from time t9 to time t10. The top and bottom input switches 550 of SH sub-circuit SH2 close at time t9 in response to the switch signal SW2A, and then open at time t10, which causes capacitor 554 to sample and hold the second magnitudes of the differential voltages on lines VP+ and VP−, which represent the intensity of the pulsed light 514 without the intensity of the ambient light 512. The time t5 to t6 ensures that the correction differential currents IC+ and IC− exist when the switch signal SW2A closes the top and bottom input switches 550 of SH sub-circuit SH2.

After this, as shown in FIG. 6F, controller 580 outputs the switch signal SW2B from time t11 to time t12. The top and bottom output switches 552 of SH sub-circuit SH2 close at time t11 in response to the switch signal SW2B, and then open at time t12, which causes the capacitor 554 to output the differential voltages on lines VP+ and VP− to buffer 560 as VS+ and VS−, which have second magnitudes that represent the second magnitudes of the differential voltages on lines VP+ and VP−, which represent the intensity of the pulsed light 514 without the intensity of the ambient light 512.

Buffer 560 reduces the second magnitudes of the sampled differential voltages VS+ and VS− by an amount defined by the pleth DC correction word CW2 to form corrected magnitudes of the sampled differential voltage VS+ and VS−, and outputs VB+ and VB− with second magnitudes that represent the corrected magnitudes of the sampled differential voltages VS+ and VS−.

A/D converter 570 digitizes the second magnitudes of the pleth signal BS to form a second digital word WD2, which represents the second magnitudes of VB+ and VB−. The second magnitudes of VB+ and VB− initially include the pleth DC component and the pleth AC component, but over time include substantially only the pleth AC component (a small pleth DC component can exist to provide an error margin). For example, A/D converter 570 can have an input range of 0V-1V.

Controller 580 determines the pleth DC correction word CW2 in response to a number of the second digital words WD2, which each includes the pleth DC component and the pleth AC component. Various conventional methods are useful to evaluate an AC signal riding on a DC level, and determine the magnitude of the DC level. For example, if the second digital words WD2 describe an AC signal that varies between 0.6V and 0.8V, then the pleth DC component is 0.6V. To provide a margin of error, the pleth DC component can be determined to be 0.59V. Controller 580 then translates the pleth DC component into the format required by the pleth DC correction word CW2.

As shown in FIG. 6G, controller 580 outputs the pleth DC correction word CW2 to buffer 560 from time t13 to time t14. D/A charge/voltage converter 562 generates and outputs VR+ and VR− in response to the pleth DC correction word CW2. The magnitudes of the correction differential charges/voltages VR+ and VR− represent the determined magnitude of the pleth DC component, e.g., 0.59V or 0.60V.

Amplifier 564 reduces the second magnitudes of VS+ and VS− by the magnitudes of VR+ and VR− to form the corrected magnitudes of the sampled differential voltages VS+ and VS−, and outputs the pleth differential voltages VB+ and VB− with second magnitudes that represent the corrected magnitudes of the sampled differential voltages VS+ and VS−. The second magnitudes of VB+ and VB− have substantially only one component, which is a pleth AC component (although a small pleth DC component can exist to provide a margin of error).

A/D converter 570 digitizes the second magnitudes of the pleth differential voltages VB+ and VB−, and outputs the second digital word WD2. After controller 580 has determined and output both the ambient DC correction word CW1 and the pleth DC correction word CW2, the second digital word WD2 substantially represents only the pleth AC component.

For example, if the pleth AC component varies between 0.6V and 0.8V before the pleth DC component and the pleth DC correction word CW2 have been determined, and the pleth DC component is determined to be 0.59V (0.01V allowance for error margin), then the pleth AC component as represented by the second digital word WD2 will vary between 0.01V and 0.21V after the pleth DC correction word CW2 has been applied.

After controller 580 has determined and applied the ambient correction word CW1 and the pleth DC correction word CW2, controller 580: (a) determines the range of the pleth AC component, such as 0.01V to 0.21V; and (b) outputs a gain signal GN to amplifier 564, which increases the gain, so that the range of the pleth AC component occupies a portion (e.g., approximately 80%) of the range of A/D converter 570. For example, if the range of A/D converter 570 is 1V and the range of the pleth AC component is 0.01V to 0.21V, then a 3× gain increases the range from 0.03V to 0.63V.

The gain increases the small pleth DC component from 0.01V to 0.03V. The increase is reflected in the second digital word WD2, which can cause the pleth DC correction word CW2 to be adjusted, which causes the pleth DC component to be further reduced. The gain can again be increased, and the process iterated a number of times as necessary until the pleth AC component occupies a desired ADC input range, such as from 0.1V to 0.9V.

Also, the transmit power can be increased, which increases the intensity of the pulsed light 514. Increasing the transmit power increases both the pleth DC component and the pleth AC component. Because gain and increased power both effect the magnitudes of the pleth DC and AC components, the gain and increased power can be independently adjusted to optimized levels.

Circuitry 500 reduces the ambient and pleth DC components such that substantially only the pleth AC component remains, and adjusts the range of the pleth AC component to substantially occupy a desired input range of A/D converter 570. The amplified pleth AC component is useful to determine biometric information (e.g., heart rate).

Figure 7:
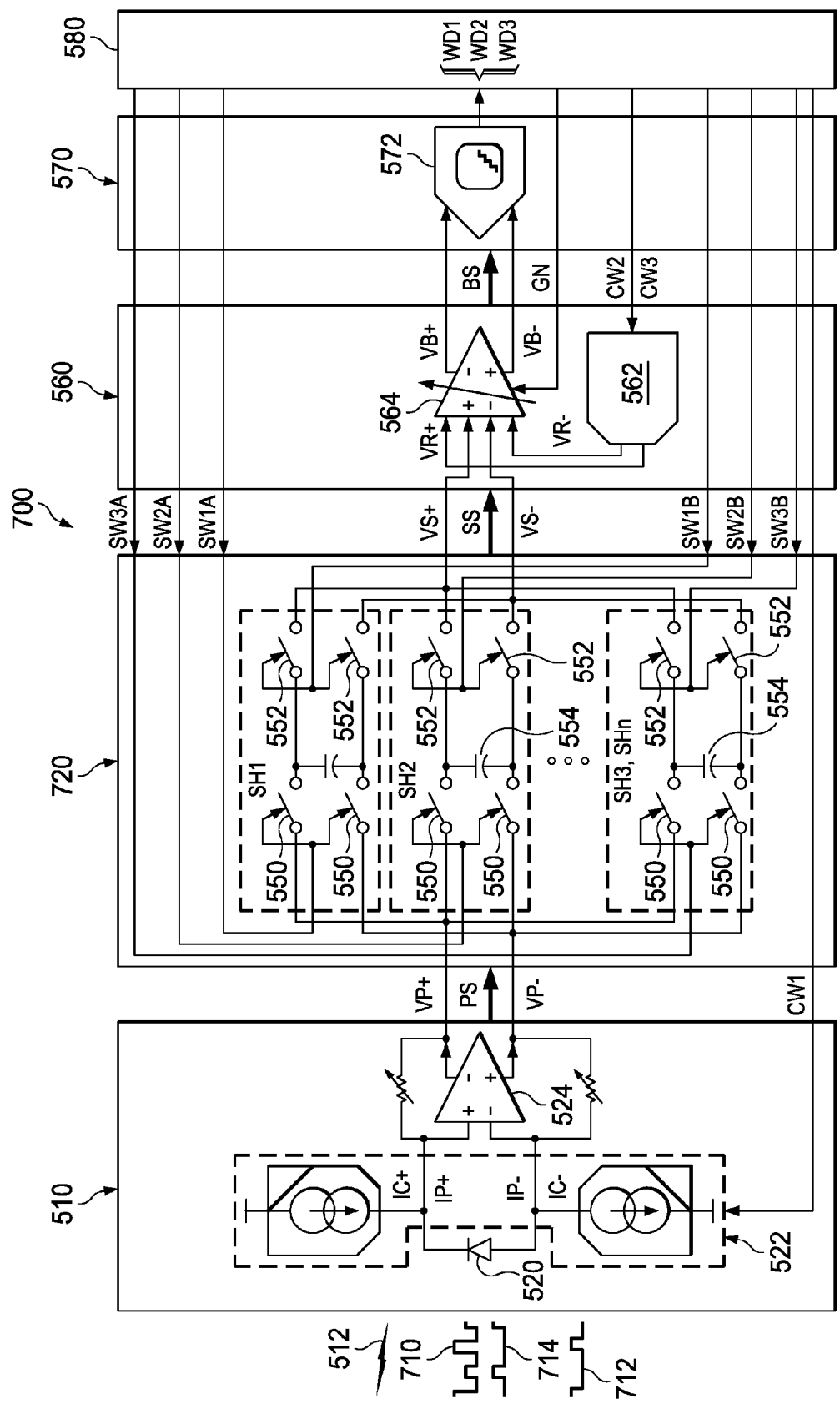
FIG. 7 is a schematic diagram of circuitry for a multi-intensity/frequency optical receiver of the example embodiments.

FIG. 7 is a schematic diagram of circuitry, indicated generally at 700, for a multi-intensity/frequency optical receiver. Circuitry 700 is similar to circuitry 500 and, as a result, uses the same reference numerals to designate the elements that are common to both circuits. Circuitry 700 can respond to: (a) an LED that transmits with two intensities; and (b) a pair of LEDS that transmit at two light frequencies, such as IR and red light.

With different intensities, photo detector 510 receives pulsed light 710, which is the same as pulsed light 514 except that pulsed light 710 alternates between two intensities. With different frequencies, photo detector 510 receives pulsed light 712, which is the same as pulsed light 514, and pulsed light 714, which is the same as pulsed light 514, except that the pulsed lights 712 and 714 have different light frequencies, such as IR and red light.

When pulsed light 710 is off, or the pulsed lights 712 and 714 are off, photo detector 510 detects the ambient intensity. When pulsed light 710 is on at a first intensity, or pulsed light 712 is on and pulsed light 714 is off, photo detector 510 detects a first pulsed intensity. When pulsed light 710 is on at a second intensity, or pulsed light 712 is off and pulsed light 714 is on, photo detector 510 detects a second pulsed intensity.

Photo detector 510 outputs the first signal on line(s) PS having a first magnitude that represents the ambient intensity, the second signal on line(s) PS having a second magnitude that represents the first pulsed intensity without the ambient intensity, and a third signal on line(s) PS having a third magnitude that represents the second pulsed intensity without the ambient intensity. The ambient intensity has a single component, which is an ambient DC intensity component. In contrast, the first pulsed intensity has three components, which are: the ambient DC intensity component, a first pleth DC intensity component, and a first pleth AC intensity component, while the second pulsed intensity has three components, which are: the ambient DC intensity component, a second pleth DC intensity component, and a second pleth AC intensity component.

Reducing the first pulsed intensity by the ambient intensity substantially removes the ambient DC intensity component from the first pulsed intensity, which leaves substantially only the first pleth DC intensity component and the first pleth AC intensity component. Photo detector 510 reduces the first pulsed intensity by the ambient intensity by reducing a magnitude, which is defined by the first pulsed intensity, by a magnitude, which is defined by the ambient DC correction word CW1, which represents the ambient intensity.

Reducing the second pulsed intensity by the ambient intensity substantially removes the ambient DC intensity component from the second pulsed intensity, which leaves substantially only the second pleth DC intensity component and the second pleth AC intensity component. Photo detector 510 reduces the second pulsed intensity by the ambient intensity by reducing a magnitude, which is defined by the second pulsed intensity, by the magnitude defined by the ambient DC correction word CW1.

The first magnitude of the first signal on line(s) PS has only one component, which is an ambient DC component. The second magnitude of the second signal on line(s) PS has substantially only two components, which are: a first pleth DC component that represents the first pleth DC intensity component, and a first pleth AC component that represents the first pleth AC intensity component. Reducing the first pulsed intensity by the ambient intensity to form the second magnitude of the second signal on line(s) PS substantially removes the ambient DC component from the second magnitude of the second signal on line(s) PS.

The third magnitude of the third signal on line(s) PS has substantially only two components, which are: a second pleth DC component that represents the second pleth DC intensity component, and a second pleth AC component that represents the second pleth AC intensity component. Reducing the second pulsed intensity by the ambient intensity to form the third magnitude of the third signal on line(s) PS substantially removes the ambient DC component from the third magnitude of the third signal on line(s) PS.

In the FIG. 7 example, photodiode 520, ambient DC correction circuit 522, and transimpedance amplifier 524 operate in the same manner as with circuitry 500, except that the differential voltages VP+ and VP− have first, second and third magnitudes that represent the first, second and third magnitudes of the first, second and third signals on line(s) PS.

As shown in FIG. 7, circuitry 700 differs from circuitry 500 in that circuitry 700 uses a demodulation circuit 720 instead of demodulation circuit 540. Demodulation circuit 720 is the same as demodulation circuit 540 except that demodulation circuit 720 also samples and holds the third magnitude of the third signal on line(s) PS, and outputs a fifth signal on line(s) SS whose magnitude represents the third magnitude of the third signal on line(s) PS.

The magnitude of the third signal on line(s) SS has an ambient DC component that represents the ambient DC component of the first signal on line(s) PS. The magnitude of the fourth signal on line(s) SS has a first pleth DC component that represents the first pleth DC component of the second signal on line(s) PS, and a first pleth AC component that represents the first pleth AC component of the second signal on line(s) PS. The magnitude of the fifth signal on line(s) SS has a second pleth DC component that represents the second pleth DC component of the third signal on line(s) PS, and a second pleth AC component that represents the second pleth AC component of the third signal on line(s) PS.

In the FIG. 7 implementation, the series of SH sub-circuits SH1-SHn in demodulation circuit 720, which are coupled to transimpedance amplifier 524, include a third SH sub-circuit SH3 in addition to the first and second SH sub-circuits SH1 and SH2. The input switches 550 and the output switches 552 of SH sub-circuit SH3 are controlled by switch signals SW3A and SW3B, respectively, which are generated and output by controller 580.

SH sub-circuit SH1 samples and holds the first magnitudes of the differential voltages on lines VP+ and VP−, and outputs VS+ and VS− with first magnitudes that represent the first magnitudes of the differential voltages on lines VP+ and VP−. SH sub-circuit SH2 samples and holds the second magnitudes of the differential voltages on lines VP+ and VP−, and outputs VS+ and VS− with second magnitudes that represent the second magnitudes of the differential voltages VP+ and VP−. SH sub-circuit SH3 samples and holds the third magnitudes of the differential voltages on lines VP+ and VP−, and outputs VS+ and VS− with third magnitudes that represent the third magnitudes of the differential voltages on lines VP+ and VP−.

Buffer 560 receives the magnitude of the third signal on line(s) SS, and outputs the pleth signal BS having a first magnitude that represents the magnitude of the third signal on line(s) SS. Buffer 560 also receives the magnitude of the fourth signal on line(s) SS, reduces the magnitude of the fourth signal on line(s) SS by a magnitude, which is defined by the pleth DC correction word CW2, and outputs the pleth signal BS having a second magnitude that represents substantially only the first pleth AC component of the fourth signal on line(s) SS (a small first pleth DC component can exist). The pleth DC correction word CW2 represents the first pleth DC component.

Buffer 560 further receives the magnitude of the fifth signal on line(s) SS, reduces the magnitude of the fifth signal on line(s) SS by a magnitude, which is defined by a pleth DC correction word CW3, and outputs the pleth signal BS with a third magnitude that represents substantially only the second pleth AC component of the fifth signal on line(s) SS (a small second pleth DC component can exist). The pleth DC correction word CW3 represents the second pleth DC component.

The first magnitude of the pleth signal BS has a single component, which is an ambient DC component. The second magnitude of the pleth signal BS has substantially only one component, which is a first pleth AC component (a small first pleth DC component can be present). Reducing the magnitude of the fourth signal on line(s) SS by the pleth DC correction word CW2 substantially removes the first pleth DC component from the second magnitude of the pleth signal BS, which leaves substantially only the first pleth AC component. Buffer 560 reduces the first pleth DC component by reducing a charge/voltage, which represents the magnitude of the fourth signal on line(s) SS, by a charge/voltage, which represents the first pleth DC component as defined by the pleth DC correction word CW2.

The third magnitude of the pleth signal BS has substantially only one component, which is a second pleth AC component (a small second pleth DC component can be present). Reducing the magnitude of the fifth signal on line(s) SS by the pleth DC correction word CW3 substantially removes the second pleth DC component from the third magnitude of the pleth signal BS, which leaves substantially only the second pleth AC component. Buffer 560 reduces the second pleth DC component by reducing a charge/voltage, which represents the magnitude of the fifth signal on line(s) SS, by a charge/voltage, which represents the second pleth DC component as defined by the pleth DC correction word CW3.

A/D converter 570 digitizes the first magnitude of the pleth signal BS to form a first digital word WD1 that represents the first magnitude of the pleth signal BS. A/D converter 570 also digitizes the second magnitude of the pleth signal BS to form a second digital word WD2 that represents the second magnitude of the pleth signal BS. A/D converter 570 further digitizes the third magnitude of the pleth signal BS to form a third digital word WD3 that represents the third magnitude of the pleth signal BS.

Controller 580 generates the ambient DC correction word CW1, which represents the ambient intensity, in response to the first digital word WD1, and outputs the ambient DC correction word CW1 to photo detector 510. Controller 580 also generates the pleth DC correction word CW2, which defines the amount that the magnitude of the fourth signal on line(s) SS is to be reduced to reduce the first pleth DC component, and outputs the pleth DC correction word CW2 to buffer 560. Controller 580 further generates the pleth DC correction word CW3, which defines the amount that the magnitude of the fifth signal on line(s) SS is to be reduced to reduce the second pleth DC component, and outputs the pleth DC correction word CW3 to buffer 560.

Figure 8A:
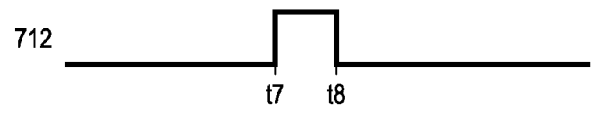
FIGS. 8A-8O are timing diagrams of an operation of the circuitry of FIG. 7.
Figure 8B:
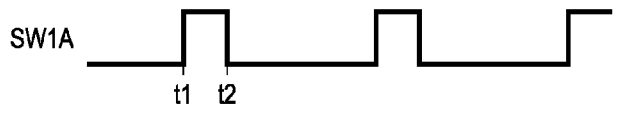
Figure 8C:
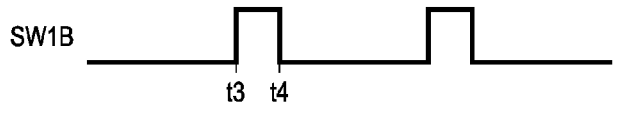
Figure 8D:
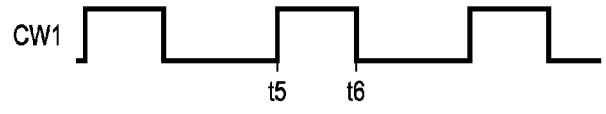
Figure 8E:
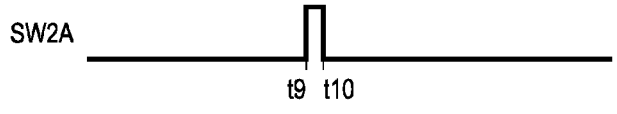
Figure 8F:
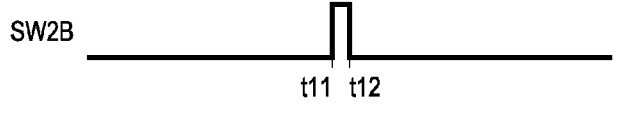
Figure 8G:
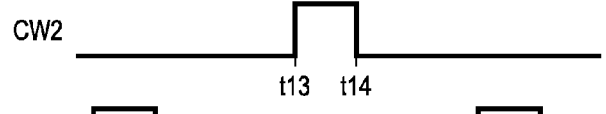
Figure 8H:
Figure 8I:
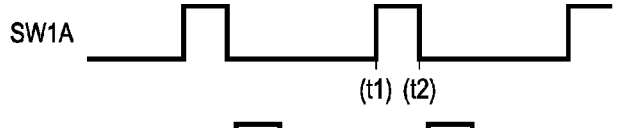
Figure 8J:
Figure 8K:
Figure 8L:
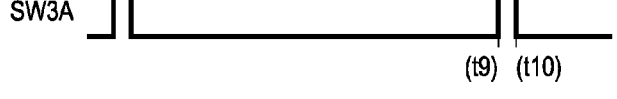
Figure 8M:
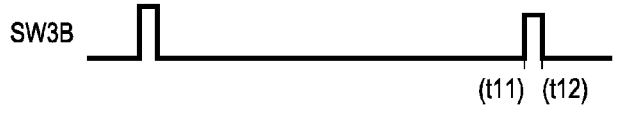
Figure 8N:
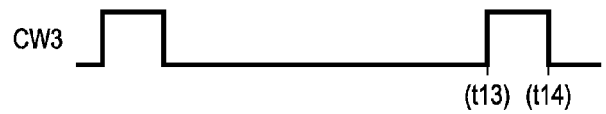
Figure 8O:

FIGS. 8A-8O are timing diagrams of an operation of the circuitry 700 of FIG. 7. FIG. 8A is a timing diagram of the pulsed light 712. FIG. 8B is a timing diagram of switch signal SW1A. FIG. 8C is a timing diagram of switch signal SW1B. FIG. 8D is a timing diagram of the ambient DC correction word CW1. FIG. 8E is a timing diagram of switch signal SW2A. FIG. 8F is a timing diagram of switch signal SW2B. FIG. 8G is a timing diagram of the pleth DC correction word CW2. FIG. 8H is a timing diagram of the pulsed light 714. FIG. 8I is a timing diagram of switch signal SW1A. FIG. 8J is a timing diagram of switch signal SW1B. FIG. 8K is a timing diagram of the ambient DC correction word CW1. FIG. 8L is a timing diagram of switch signal SW3A. FIG. 8M is a timing diagram of switch signal SW3B. FIG. 8N is a timing diagram the pleth DC correction word CW3. FIG. 8O is a timing diagram of the pulsed light 710.

As shown in FIGS. 8A-8O, circuitry 700 operates the same as circuitry 500, but with two frequencies instead of one. As further shown in FIGS. 8A-8N, the pulses of pulsed light 712 and pulsed light 714, along with the switching signals and correction words, are interleaved. FIGS. 8A-8G are the same as FIGS. 6A-6G, while the timing of FIGS. 8H-8N with respect to pulsed light 714 is the same as the timing of FIGS. 6A-6G with respect to pulsed light 514.

Ambient SH sub-circuit SH1 continuously holds the first magnitudes of the differential voltages on lines VP+ and VP− that result from the off times of the pulsed lights 712 and 714. SH sub-circuit SH2 continuously holds the second magnitudes of the differential voltages on lines VP+ and VP− that result from pulsed light 712, while SH sub-circuit SH3 continuously holds the third magnitudes of the differential voltages on lines VP+ and VP− that result from pulsed light 714.

Also, circuitry 700 can operate the same when two intensities are used instead of two frequencies. In the FIG. 8O example, the pulses of pulsed light 710 that have a first intensity occur at the same time that the pulses in pulsed light 712 occur, while the pulses of pulsed light 710 that have a second intensity occur at the same time that the pulses in pulsed light 714 occur. Circuitry 700 can process the first intensity pulses in the same manner that the pulses in pulsed light 712 are processed, while circuitry 700 can process the second intensity pulses in the same manner that the pulses in pulsed light 714 are processed.

In this example, circuitry 500 and 700 continuously update the ambient DC correction word CW1, the pleth DC correction word CW2, and the pleth DC correction word CW3 to capture changes as the ambient DC components and the pleth DC components drift over time. Alternately, the ambient DC correction word CW1, the pleth DC correction word CW2, and the pleth DC correction word CW3 can be updated periodically.

Circuitry 700 reduces the ambient and first pleth DC components such that substantially only the first pleth AC component remains, and adjusts the range of the first pleth AC component to substantially occupy a desired input range of A/D converter 570. The amplified first pleth AC component is useful to determine biometric information (e.g., heart rate).

Also, circuitry 700 reduces the ambient and second pleth DC components such that substantially only the second pleth AC component remains, and adjusts the range of the second pleth AC component to substantially occupy a desired input range of A/D converter 570. For example, the amplified second pleth AC component and the amplified first pleth AC component are useful to determine changes in the volume of arterial blood (which can be used for determining the oxygen saturation level (SpO2)). Further, the changes in the pleth DC component over time can also be measured to determine other conditions.

Although the FIG. 7 example illustrates a multi-intensity/frequency circuitry 700 that processes two intensities or two frequencies, additional intensities or frequencies can be processed by increasing the number of SH sub-circuits SH1-SHn within circuitry 700. Further, additional photodiodes can be included. For example, two spaced-apart photodiodes can capture nearly the same photo information, which when compared is useful to determine motion.

Figure 9:
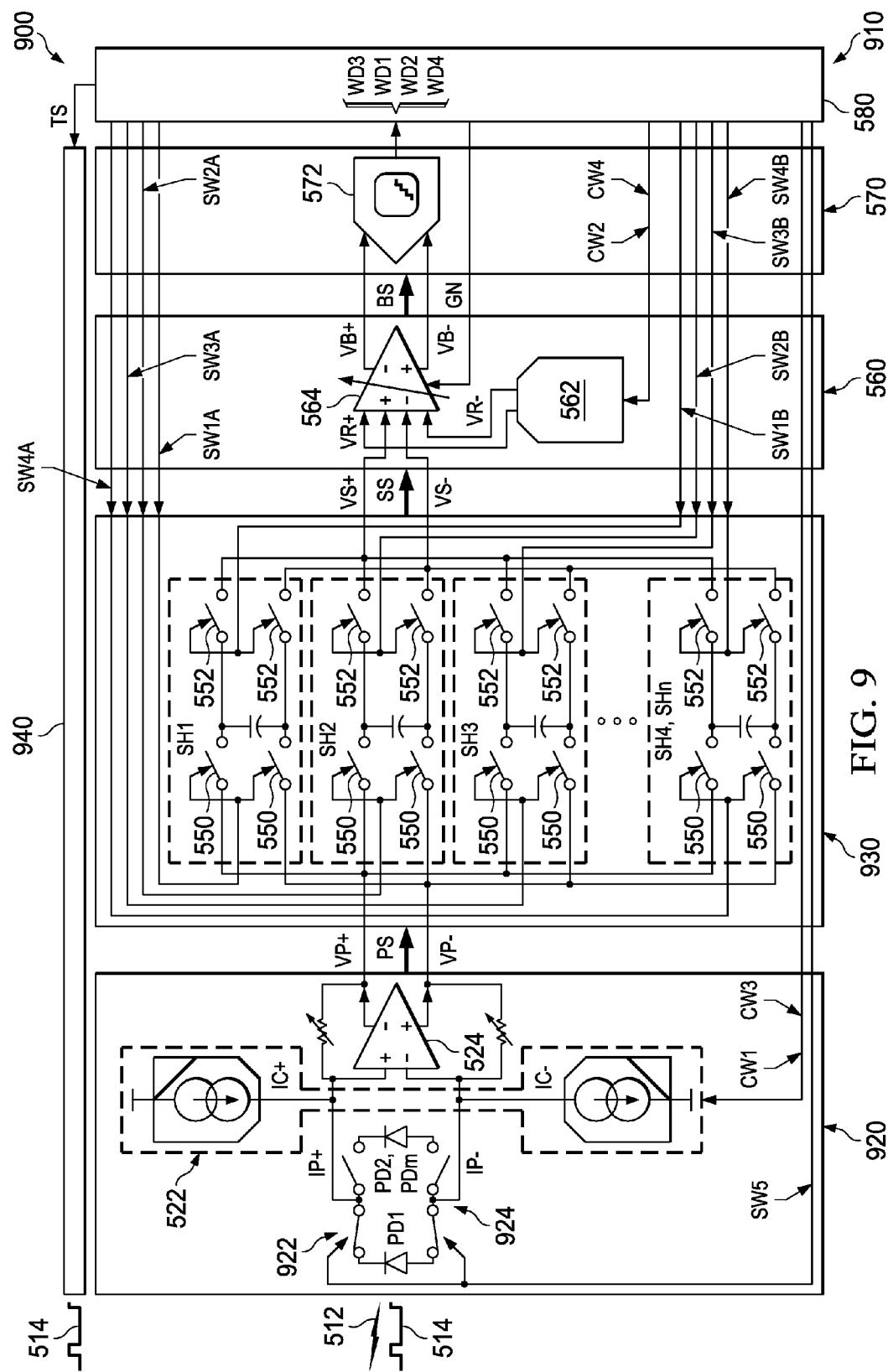
FIG. 9 is a schematic diagram of circuitry for a photoplethysmograph ("PPG") 900 of the example embodiments.

FIG. 9 is a schematic diagram of circuitry, indicated generally at 900, for a photoplethysmograph ("PPG"). PPG 900 includes an optical receiver 910. Optical receiver 910 is similar to circuitry 500 and, as a result, uses the same reference numerals to designate the structures that are common to both.

As shown in FIG. 9, optical receiver 910 differs from circuitry 500 in that optical receiver 910 uses a photo detector 920 instead of photo detector 510. Photo detector 920 is the same as photo detector 510 except that photo detector 920 detects a first ambient intensity, a first pulsed intensity, a second ambient intensity, and a second pulsed intensity.

Also, photo detector 920 generates and outputs the first signal on line(s) PS having a first magnitude that represents the first ambient intensity, a second signal on line(s) PS having a second magnitude that represents the first pulsed intensity without the first ambient intensity (the first pulsed intensity minus the first ambient intensity), a third signal on line(s) PS having a third magnitude that represents the second ambient intensity, and a fourth signal on line(s) PS having a fourth magnitude that represents the second pulsed intensity without the second ambient intensity (the second pulsed intensity minus the second ambient intensity).

The first magnitude of the first signal on line(s) PS has a single component, which is a first ambient DC component that represents the first ambient DC intensity component. The second magnitude of the second signal on line(s) PS has substantially only two components, which are: a first pleth DC component that represents the first pleth DC intensity component, and a first pleth AC component that represents the first pleth AC intensity component. Reducing the first pulsed intensity by the first ambient intensity to form the second magnitude of the second signal on line(s) PS substantially removes the first ambient DC intensity component from the second magnitude of the second signal on line(s) PS.

The third magnitude of the third signal on line(s) PS has a single component, which is a second ambient DC component that represents the second ambient DC intensity component. The fourth magnitude of the fourth signal on line(s) PS has substantially only two components, which are: a second pleth DC component that represents the second pleth DC intensity component, and a second pleth AC component that represents the second pleth AC intensity component. Reducing the second pulsed intensity by the second ambient intensity to form the fourth magnitude of the fourth signal on line(s) PS substantially removes the second ambient DC intensity component from the fourth magnitude of the fourth signal on line(s) PS.

In the implementation illustrated in FIG. 9, photo detector 920 differs from photo detector 510 in that photo detector 920 includes a series of photodiodes PD1-PDm instead of the single photodiode 520 in photo detector 510. In the FIG. 9 example, two photodiodes PD1 and PD2 are shown. The photodiodes PD1 and PD2 both receive ambient light 512 and pulsed light 514, and are physically spaced apart.

Photo detector 920 also includes a pair of switches 922 and 924 that are coupled to the photo diodes PD1 and PD2 and transimpedance amplifier 524. The switches 922 and 924 connect either photo diode PD1 or photo diode PD2 to transimpedance amplifier 524, and respond to a switch signal SW5 that is generated and output by controller 580.

Optical receiver 910 also differs from circuitry 500 in that optical receiver 910 uses a demodulation circuit 930 instead of demodulation circuit 540. Demodulation circuit 930 is the same as demodulation circuit 540 except that demodulation circuit 930 also samples and holds the third and fourth magnitudes of the third and fourth signals on line(s) PS, and outputs fifth and sixth signals on line(s) SS whose magnitudes represent the third and fourth magnitudes of the third and fourth signals on line(s) PS, respectively.

The magnitude of the third signal on line(s) SS has a first ambient DC component that represents the first ambient DC component of the first signal on line(s) PS. The magnitude of the fourth signal on line(s) SS has a first pleth DC component that represents the first pleth DC component of the second signal on line(s) PS, and a first pleth AC component that represents the first pleth AC component of the second signal on line(s) PS.

The magnitude of the fifth signal on line(s) SS has a second ambient DC component that represents the second ambient DC component of the third signal on line(s) PS. The magnitude of the sixth signal on line(s) SS has a second pleth DC component that represents the second pleth DC component of the fourth signal on line(s) PS, and a second pleth AC component that represents a second pleth AC component of the fourth signal on line(s) PS.

In the FIG. 9 implementation, the series of SH sub-circuits SH1-SHn in demodulation circuit 930, which are coupled to transimpedance amplifier 524, additionally include a third SH sub-circuit SH3 and a fourth SH sub-circuit SH4. The input switches 550 and the output switches 552 of SH sub-circuit SH3 are controlled by switch signals SW3A and SW3B, respectively, which are generated and output by controller 580. The input switches 550 and the output switches 552 of SH sub-circuit SH4 are controlled by switch signals SW4A and SW4B, respectively, which are generated and output by controller 580.

In the FIG. 9 example, the photodiodes PD1 and PD2, ambient DC correction circuit 522, and transimpedance amplifier 524 operate in the same manner as with circuitry 500, except that the differential voltages VP+ and VP− have first, second, third and fourth magnitudes that represent the first, second, third and fourth magnitudes of the first, second, third and fourth signals on line(s) PS.

SH sub-circuit SH1 samples and holds the first magnitudes of the differential voltages on lines VP+ and VP−, and outputs VS+ and VS− having first magnitudes that represent the first magnitudes of the differential voltages on lines VP+ and VP−. SH sub-circuit SH2 samples and holds the second magnitudes of the differential voltages on lines VP+ and VP−, and outputs VS+ and VS− with second magnitudes that represent the second magnitudes of the differential voltages on lines VP+ and VP−.

SH sub-circuit SH3 samples and holds the third magnitudes of the differential voltages VP+ and VP−, and outputs VS+ and VS− having third magnitudes that represents the third magnitudes of the differential voltages on lines VP+ and VP−. SH sub-circuit SH4 samples and holds the fourth magnitudes of the differential voltages VP+ and VP−, and outputs VS+ and VS− having fourth magnitudes that represent the fourth magnitudes of the differential voltages on lines VP+ and VP−.

Buffer 560 receives the magnitude of the third signal on line(s) SS, and outputs the pleth signal BS having a first magnitude that represents the third magnitude of the third signal on line(s) SS. Buffer 560 also receives the magnitude of the fourth signal on line(s) SS, reduces the magnitude of the fourth signal on line(s) SS by a magnitude, which is defined by the pleth DC correction word CW2, and outputs the pleth signal BS having a second magnitude that represents substantially only the first pleth AC component of the fourth signal on line(s) SS. The pleth DC correction word CW2 represents the first pleth DC component.

Also, buffer 560 receives the magnitude of the fifth signal on line(s) SS, and outputs the pleth signal BS having a third magnitude that represents the magnitude of the fifth signal on line(s) SS. Buffer 560 also receives the magnitude of the sixth signal on line(s) SS, reduces the magnitude of the sixth signal on line(s) SS by a magnitude, which is defined by the pleth DC correction word CW3, and outputs the pleth signal BS having a fourth magnitude that represents substantially only the second pleth AC component of the sixth signal on line(s) SS. The pleth DC correction word CW3 represents the second pleth DC component.

A/D converter 570 digitizes the first magnitude of the pleth signal BS to form a first digital word WD1 that represents the first magnitude of the pleth signal BS. A/D converter 570 also digitizes the second magnitude of the pleth signal BS to form a second digital word WD2 that represents the second magnitude of the pleth signal BS. A/D converter 570 further digitizes the third magnitude of the pleth signal BS to form a third digital word WD3 that represents the third magnitude of the pleth signal BS. A/D converter 570 additionally digitizes the fourth magnitude of the pleth signal BS to form a fourth digital word WD4 that represents the fourth magnitude of the pleth signal BS.

Controller 580 generates the ambient DC correction word CW1, which represents the first ambient intensity, in response to the first digital word WD1, and outputs the ambient DC correction word CW1 to photo detector 510. Controller 580 also generates the pleth DC correction word CW2, which defines the amount that the magnitude of the fourth signal on line(s) SS is to be reduced to reduce the first pleth DC component, and outputs the pleth DC correction word CW2 to buffer 560.

Controller 580 further generates the ambient DC correction word CW3, which represents the second ambient intensity, in response to the third digital word WD3, and outputs the ambient DC correction word CW3 to photo detector 510. Controller 580 also generates the pleth DC correction word CW4, which defines the amount that the magnitude of the sixth signal on line(s) SS is to be reduced to reduce the second pleth DC component, and outputs the pleth DC correction word CW4 to buffer 560.

Figure 10A:
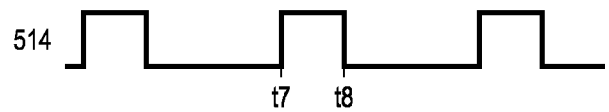
FIGS. 10A-10N are timing diagrams of an operation of the circuitry of FIG. 9.
Figure 10B:
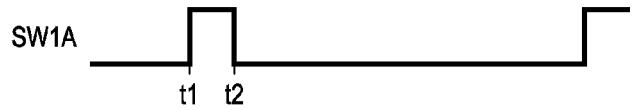
Figure 10C:
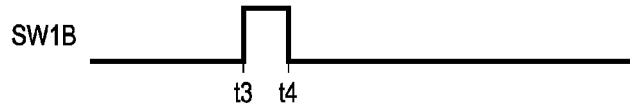
Figure 10D:
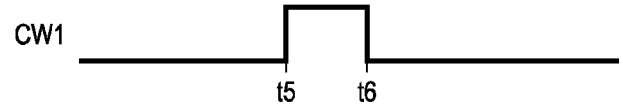
Figure 10E:
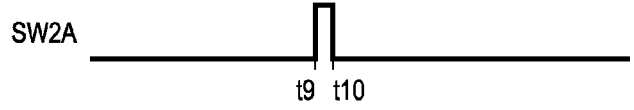
Figure 10F:
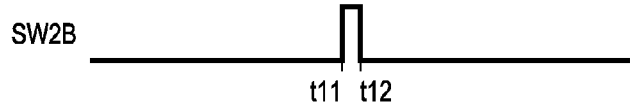
Figure 10G:
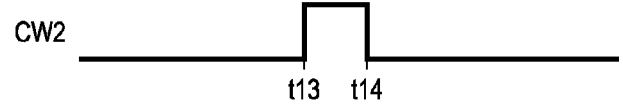
Figure 10H:
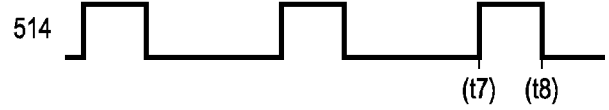
Figure 10I:
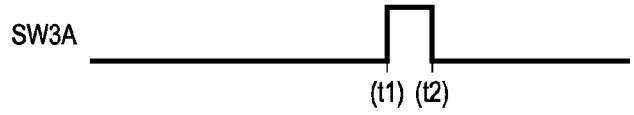
Figure 10J:
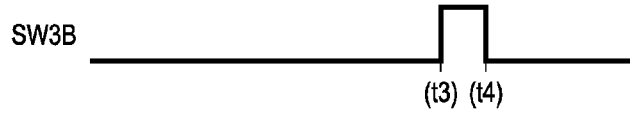
Figure 10K:
Figure 10L:
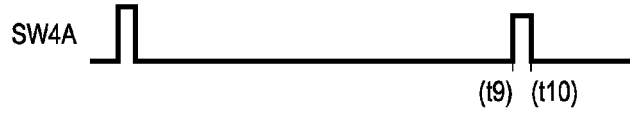
Figure 10M:
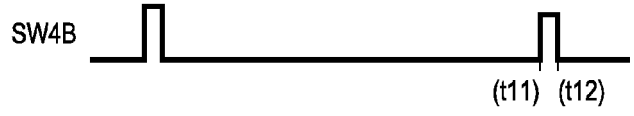
Figure 10N:
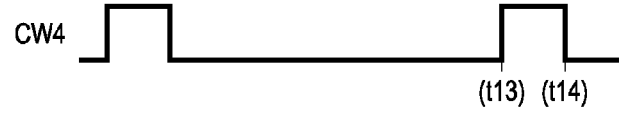

FIGS. 10A-10N are timing diagrams of an operation of circuitry 900 of FIG. 9. FIG. 10A is a timing diagram of the pulsed light 514. FIG. 10B is a timing diagram of switch signal SW1A. FIG. 10C is a timing diagram of switch signal SW1B. FIG. 10D is a timing diagram of the ambient DC correction word CW1. FIG. 10E is a timing diagram of switch signal SW2A. FIG. 10F is a timing diagram of switch signal SW2B. FIG. 10G is a timing diagram of the pleth DC correction word CW2. FIG. 10H is a timing diagram of the pulsed light 514. FIG. 10I is a timing diagram of switch signal SW3A. FIG. 10J is a timing diagram of switch signal SW3B. FIG. 10K is a timing diagram of the ambient DC correction word CW3. FIG. 10L is a timing diagram of switch signal SW4A. FIG. 10M is a timing diagram of switch signal SW4B. FIG. 10N is a timing diagram the pleth DC correction word CW4.

As shown in FIGS. 10A-10N, circuitry 900 operates the same as circuitry 500, but with two photodiodes instead of one. As further shown in FIGS. 10A-10N, the pulses of pulsed light 514, along with the switching signals and correction words, are interleaved between the two photodiodes. FIGS. 10A-10G, which illustrate photodiode PD1, are the same as FIGS. 6A-6G, while FIGS. 10H-10N, which illustrate photodiode PD2, are the same as the timing of FIGS. 6A-6G.

The first and second ambient levels as defined by the digital words WD1 and WD3, and the first and second pleth AC levels as defined by the digital words WD2 and WD4, can be compared. For example, when the photodiodes PD1 and PD2 are spaced apart, differences between the first and second ambient DC levels and/or the first and second pleth AC levels are useful to detect motion.

Referring back to FIG. 9, PPG 900 also includes an optical transmitter 940 that transmits pulsed light 514. Controller 580 generates and outputs a transmission signal TS that controls the transmission timing of pulsed light 514 and the transmission power levels of pulsed light 514. (Optical transmitter 940 can also be used with circuitry 500. An optical transmitter that outputs pulsed light 710 or the pulsed lights 712 and 714 can also be used with circuitry 700.) PPG 900 illustrates the use of multiple photodiodes, multiple SH sub-circuits, and a transmitter.

One of the advantages of the circuits 500, 700, and 910 is that, in addition to substantially reducing the ambient and pleth DC components, both the ambient DC component and the pleth DC components can be individually controlled, without impact or dependence on the pleth AC component. Reduction in the ambient DC component is unrelated to any reduction in the pleth DC component or the pleth AC component.

Another advantage of the circuits 500, 700, and 910 is that the pleth DC and AC components can be adjusted by way of changing the gain or the transmit power level. An optimum range of the pleth AC signal can be input to the A/D converter by removing the ambient DC component, removing the pleth DC component, and adjusting the gain and transmit power level. This allows for greater controllability and optimization of the SNR of the receive chain.

Modifications are possible in the described embodiments, and other embodiments are possible, within the scope of the claims.

What is claimed is:

1. Circuitry for an optical receiver, comprising:
   a photo detector to:
      receive ambient light that has an ambient intensity and, in response thereto, output a first signal on at least one first line having a first magnitude that represents the ambient intensity; and
      receive pulsed light that has a pulsed intensity and, in response thereto, output a second signal on the at least one first line having a second magnitude that represents the pulsed intensity without the ambient intensity, the second magnitude of the second signal having a pleth DC component and a pleth AC component; and
   a demodulation circuit coupled to the photo detector to:
      sample and hold the first signal, and output a third signal on at least one second line whose magnitude represents the first magnitude of the first signal; and sample and hold the second signal, and output a fourth signal on the at least one second line whose magnitude represents the second magnitude of the second signal, the magnitude of the fourth signal having a pleth DC component that represents the pleth DC component of the second signal, and a pleth AC component that represents the pleth AC component of the second signal.

2. The circuitry of claim 1 and further comprising a buffer coupled to the demodulation circuit, the buffer to:
receive the magnitude of the third signal, and output a pleth signal having a first magnitude that represents the magnitude of the third signal; and
receive the magnitude of the fourth signal, reduce the pleth DC component of the magnitude of the fourth signal by a defined amount to form the pleth signal having a second magnitude, and output the pleth signal having the second magnitude.

3. The circuitry of claim 2 and further comprising an analog-to-digital (A/D) converter coupled to the buffer, the A/D converter to:
digitize the first magnitude of the pleth signal to form a first digital word that represents the first magnitude of the pleth signal; and
digitize the second magnitude of the pleth signal to form a second digital word that represents the second magnitude of the pleth signal.

4. The circuitry of claim 3 and further comprising a controller coupled to the A/D converter, the photo detector, and the buffer, the controller to:
generate an ambient DC correction word that represents the ambient intensity in response to the first digital word, and output the ambient DC correction word to the photo detector; and
generate a pleth DC correction word that represents the defined amount in response to the second digital word, and output the pleth DC correction word to the buffer.

5. The circuitry of claim 4 wherein the photo detector is to generate the magnitude of the second signal by reducing a magnitude that represents the pulsed intensity by a magnitude that represents the ambient intensity as defined by the ambient DC correction word.

6. The circuitry of claim 4 wherein the buffer is to generate the second magnitude of the pleth signal by reducing a magnitude that represents the magnitude of the fourth signal by a magnitude that represents the pleth DC component as defined by the pleth DC correction word.

7. The circuitry of claim 4 wherein the photo detector includes:
a photo diode to generate a pair of IP differential currents having first magnitudes that vary in response to variations in the ambient intensity, and second magnitudes that vary in response to variations in the pulsed intensity;
an ambient DC correction circuit coupled to the photo diode to source and sink a pair of correction differential currents in response to the ambient DC correction word, the pair of correction differential currents combine with the pair of IP differential currents to reduce the second magnitudes of the pair of IP differential currents by an amount determined from the ambient DC correction word to form corrected magnitudes for the pair of IP differential currents; and
a transimpedance amplifier coupled to the ambient DC correction circuit to convert the pair of IP differential currents into a pair of VP differential voltages with first magnitudes that represent the first magnitudes of the pair of IP differential currents, and second magnitudes that represent the corrected magnitudes of the pair of IP differential currents.

8. The circuitry of claim 7 wherein the ambient DC correction circuit includes a pair of digital-to-analog (D/A) converters to receive the ambient DC correction word, and convert the ambient DC correction word into the pair of correction differential currents.

9. The circuitry of claim 7 wherein the first and second signals are output as the pair of VP differential voltages.

10. The circuitry of claim 7 wherein the demodulation circuit includes:
a first SH sub-circuit to sample and hold the first magnitudes of the pair of VP differential voltages, and output a pair of sampled differential voltages having first magnitudes that represent the first magnitudes of the pair of VP differential voltages, and
a second SH sub-circuit coupled to the first SH sub-circuit to sample and hold the second magnitudes of the pair of VP differential voltages, and output the pair of sampled differential voltages with second magnitudes that represents the second magnitudes of the pair of VP differential voltages.

11. The circuitry of claim 10 wherein the third and fourth signals are output as the pair of sampled differential voltages.

12. The circuitry of claim 10 wherein the buffer includes:
a D/A charge/voltage converter to generate a pair of correction differential charges/voltages having magnitudes in response to the pleth DC correction word; and
an amplifier coupled to the D/A charge/voltage converter to:
amplify the first magnitudes of the pair of sampled differential voltages to form the first magnitudes of a pair of pleth differential voltages; and
reduce a first value that represents the second magnitudes of the pair of sampled differential voltages by a second value that represents the magnitudes of the pair of correction differential charges/voltages to form the second magnitudes of the pair of pleth differential voltages.

13. The circuitry of claim 12 wherein the pleth signal is output as the pair of pleth differential voltages.

14. The circuitry of claim 1 wherein the pulsed intensity of the pulsed light includes a first pulsed intensity and a second pulsed intensity.

15. The circuitry of claim 1 wherein the photo detector includes two photodiodes.

16. The circuitry of claim 1 wherein
the photo detector to:
receive ambient light that has a second ambient intensity, and output a third signal on at least one first line having a third magnitude that represents the second ambient intensity; and
receive pulsed light that has a second pulsed intensity, and output a fourth signal on the at least one first line having a fourth magnitude that represents the second pulsed intensity without the second ambient intensity, the fourth magnitude of the fourth signal having a pleth DC component and a pleth AC component; and
the demodulation circuit to:
sample and hold the third magnitude of the third signal on the at least one first line, and output a fifth signal on the at least one second line whose magnitude represents the third magnitude of the third signal on the at least one first line, and sample and hold the fourth magnitude of the fourth signal on the at least one first line, and output a sixth signal on the at least one second line whose magnitude represents the fourth magnitude of the fourth signal on the at least one first line, the magnitude of the sixth signal on the at least one second line having a pleth DC component and a pleth AC component.

17. The circuitry of claim 16 wherein the buffer is to:
receive the magnitude of the fifth signal on the at least one second line, and outputs the pleth signal having a third magnitude that represents the magnitude of the fifth signal on the at least one second line; and
receive the magnitude of the sixth signal on the at least one second line, reduce the pleth DC component in the magnitude of the sixth signal by a defined amount to form the pleth signal with a fourth magnitude, and outputs the pleth signal having the fourth magnitude.

18. A method of operating circuitry for an optical receiver, the method comprising:
receiving ambient light that has an ambient intensity and, in response thereto, outputting a first signal having a first magnitude that represents the ambient intensity;
receiving pulsed light that has a pulsed intensity and, in response thereto, outputting a second signal having a second magnitude that represents the pulsed intensity without the ambient intensity, the second magnitude of the second signal having a pleth DC component and a pleth AC component;
sampling and holding the first magnitude of the first signal, and outputting a third signal having a magnitude that represents the first magnitude of the first signal; and
sampling and holding the second magnitude of the second signal, and outputting a fourth signal with a magnitude that represents the second magnitude of the second signal, the magnitude of the fourth signal having a pleth DC component that represents the pleth DC component of the second signal, and a pleth AC component that represents the pleth AC component of the second signal.

19. The method of claim 18 and further comprising:
receiving the magnitude of the third signal, and outputting a pleth signal having a magnitude that represents the magnitude of the third signal; and
receiving the magnitude of the fourth signal, reducing the pleth DC component of the magnitude of the fourth signal by a defined amount to form the pleth signal with a second magnitude, and outputting the pleth signal having the second magnitude.

20. The method of claim 19 and further comprising:
digitizing the first magnitude of the pleth signal to form a first digital word that represents the first magnitude of the pleth signal; and
digitizing the second magnitude of the pleth signal to form a second digital word that represents the second magnitude of the pleth signal.

* * * * *